US009504524B2

(12) United States Patent
Behnke, II

(10) Patent No.: US 9,504,524 B2
(45) Date of Patent: Nov. 29, 2016

(54) TISSUE IMPEDANCE MEASUREMENT USING A SECONDARY FREQUENCY

(71) Applicant: COVIDIEN LP, Mansfield, MA (US)

(72) Inventor: Robert J. Behnke, II, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 156 days.

(21) Appl. No.: 13/943,452

(22) Filed: Jul. 16, 2013

(65) Prior Publication Data
US 2013/0338661 A1    Dec. 19, 2013

Related U.S. Application Data

(60) Continuation of application No. 13/568,679, filed on Aug. 7, 2012, now Pat. No. 8,486,057, which is a division of application No. 12/468,718, filed on May 19, 2009, now Pat. No. 8,246,615.

(51) Int. Cl.
A61B 18/18    (2006.01)
A61B 18/14    (2006.01)
(Continued)

(52) U.S. Cl.
CPC ............ *A61B 18/18* (2013.01); *A61B 18/1815* (2013.01); *A61B 18/1477* (2013.01); *A61B 2017/00026* (2013.01); *A61B 2018/00702* (2013.01); *A61B 2018/00875* (2013.01);
(Continued)

(58) Field of Classification Search
CPC ............... A61B 2018/1273; A61B 2018/128; A61B 2018/1425; A61B 2018/1869; A61B 2018/1876; A61B 2018/1838
USPC .......... 606/33, 41, 42, 34; 607/99, 101, 105, 607/156
See application file for complete search history.

(56) References Cited

U.S. PATENT DOCUMENTS

| D223,367 S | 4/1972 | Kountz |
| D263,020 S | 2/1982 | Rau, III |
| D266,842 S | 11/1982 | Villers et al. |

(Continued)

FOREIGN PATENT DOCUMENTS

| CN | 1103807 A | 6/1995 |
| DE | 390937 C | 3/1924 |

(Continued)

OTHER PUBLICATIONS

European Search Report EP 08004975 dated Jul. 24, 2008.
(Continued)

*Primary Examiner* — Michael Peffley
*Assistant Examiner* — Thomas Giuliani

(57) ABSTRACT

A microwave ablation system includes a generator including a first energy source, a second energy source and a diplexer, the diplexer multiplexes a first energy from the first energy source and a second energy from the second energy source. The system also includes a cable including a center conductor and an outer sheath where the multiplexed energy is transmitted through the center conductor. In addition an antenna is provided that is operable to receive the multiplexed energy from the center conductor and to deliver the multiplexed energy to a region of tissue. The outer sheath acts as a return path of the second energy to the second energy source. A sensor is also provided that measures at least one parameter of the second energy generated by the second energy source and the second energy returned from the region of tissue.

5 Claims, 8 Drawing Sheets

(51) Int. Cl.
*A61B 17/00* (2006.01)
*A61B 18/00* (2006.01)

(52) U.S. Cl.
CPC *A61B2018/1425* (2013.01); *A61B 2018/1869* (2013.01); *A61B 2018/1876* (2013.01)

(56) References Cited

U.S. PATENT DOCUMENTS

| | | |
|---|---|---|
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,817,093 A | 10/1998 | Williamson, IV et al. |
| 6,033,399 A | 3/2000 | Gines |
| D424,693 S | 5/2000 | Pruter |
| D424,694 S | 5/2000 | Tetzlaff et al. |
| D425,201 S | 5/2000 | Tetzlaff et al. |
| 6,224,593 B1 | 5/2001 | Ryan et al. |
| 6,245,065 B1 | 6/2001 | Panescu et al. |
| D449,886 S | 10/2001 | Tetzlaff et al. |
| D457,958 S | 5/2002 | Dycus et al. |
| D457,959 S | 5/2002 | Tetzlaff et al. |
| 6,398,779 B1 | 6/2002 | Buysse et al. |
| 6,569,159 B1* | 5/2003 | Edwards et al. .......... 606/41 |
| 6,632,221 B1 | 10/2003 | Edwards et al. |
| 6,632,222 B1 | 10/2003 | Edwards et al. |
| 6,641,580 B1 | 11/2003 | Edwards et al. |
| 6,645,198 B1 | 11/2003 | Bommannan et al. |
| D487,039 S | 2/2004 | Webster et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,118,808 B2* | 2/2012 | Smith ............... A61B 18/18 606/27 |
| 8,246,615 B2* | 8/2012 | Behnke ................ 606/33 |
| 8,480,666 B2 | 7/2013 | Buysse et al. |
| 8,486,057 B2 | 7/2013 | Behnke, II |
| 8,512,329 B2 | 8/2013 | Paulus |
| 8,832,927 B2* | 9/2014 | Smith ............... A61B 18/18 29/594 |
| 2002/0165530 A1 | 11/2002 | Harano et al. |
| 2003/0088242 A1* | 5/2003 | Prakash ............. A61B 18/18 606/33 |
| 2003/0120269 A1* | 6/2003 | Bessette et al. .......... 606/32 |
| 2003/0158551 A1 | 8/2003 | Paton et al. |
| 2003/0195499 A1* | 10/2003 | Prakash et al. .......... 606/33 |
| 2005/0004570 A1 | 1/2005 | Chapman et al. |
| 2005/0101948 A1 | 5/2005 | Harano et al. |
| 2005/0101951 A1 | 5/2005 | Wham et al. |
| 2005/0149010 A1* | 7/2005 | Turovskiy ......... A61B 18/18 606/33 |
| 2008/0154259 A1 | 6/2008 | Gough et al. |
| 2008/0234574 A1* | 9/2008 | Hancock ............ A61B 5/0507 600/430 |
| 2012/0192063 A1 | 7/2012 | Koren |
| 2012/0239024 A1 | 9/2012 | Ladtkow et al. |
| 2012/0239030 A1 | 9/2012 | Ladtkow |
| 2012/0253341 A1 | 10/2012 | Paulus |
| 2012/0259324 A1 | 10/2012 | Brannan |
| 2012/0259328 A1 | 10/2012 | Rossetto et al. |
| 2012/0259329 A1 | 10/2012 | Decarlo |
| 2012/0271306 A1 | 10/2012 | Buysse et al. |
| 2012/0271307 A1 | 10/2012 | Prakash et al. |
| 2012/0277738 A1 | 11/2012 | Rossetto et al. |
| 2012/0303014 A1 | 11/2012 | Prakash et al. |
| 2012/0303018 A1 | 11/2012 | Ladtkow et al. |
| 2012/0304463 A1 | 12/2012 | Buysse |
| 2012/0310228 A1 | 12/2012 | Bonn et al. |
| 2012/0325516 A1 | 12/2012 | Bonn |
| 2012/0330302 A1 | 12/2012 | Willyard |
| 2013/0030429 A1 | 1/2013 | Rusin |
| 2013/0041362 A1 | 2/2013 | Lee et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0178841 A1 | 7/2013 | Reid, Jr. |
| 2013/0178842 A1 | 7/2013 | Reid, Jr. |
| 2013/0178843 A1 | 7/2013 | Lee et al. |
| 2013/0178844 A1 | 7/2013 | Lee et al. |
| 2013/0218143 A1 | 8/2013 | Ross |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 694291 A1 | 1/1996 |
| EP | 0 836 868 A2 | 4/1998 |
| EP | 0 882 955 A1 | 12/1998 |
| EP | 1 159 926 A2 | 12/2001 |
| EP | 1472984 | 11/2004 |
| FR | 179 607 | 11/1906 |
| FR | 1 275 415 A | 11/1961 |
| FR | 1 347 865 A | 1/1964 |
| FR | 2 235 669 A1 | 1/1975 |

(56) References Cited

FOREIGN PATENT DOCUMENTS

| | | |
|---|---|---|
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 96/39086 A1 | 12/1996 |
| WO | 00/36985 A2 | 6/2000 |
| WO | 2005/115235 A1 | 12/2005 |
| WO | 2008/043999 A2 | 4/2008 |
| WO | 2008/044013 A2 | 4/2008 |
| WO | 2010/035831 A1 | 4/2010 |

OTHER PUBLICATIONS

European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 extended dated Jul. 6, 2010.
European Search Report EP 09151621 dated Jun. 18, 2009.
European Search Report EP 09156861.8 extended dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok. TM. Breast Lesion Needle/ Wire Localizer, Namic.RTM. Angiographic Systems Division, Glens Falls, New York, (Hospital products price list), 4 pages.

(56) References Cited

OTHER PUBLICATIONS

Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure. TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure. TM."Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndotHill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure. TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12; pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure. TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure. TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure. TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure. TM. System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure. TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.

(56) References Cited

OTHER PUBLICATIONS

McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure. TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure. TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure. TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Longterm Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis. TM. Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.

(56) References Cited

OTHER PUBLICATIONS

European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10180964.8 dated Dec. 22, 2012.
European Search Report EP 10180965.6 dated Jan. 26, 2011.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
ValleyLab Brochure, "Electosurgery: A Historical Overview", Innovations in Electrosurgery, 1999.
Vallfors et al., "Automatically Controlled Bipolar Electrocoagulation—'Coa-Comp'" Neurosurgical Review 7:2-3 (1984) pp. 187-190.
W. Scott Helton, "LigaSure. TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/853,363, filed Mar. 29, 2013, Kim.
U.S. Appl. No. 13/856,363, filed Apr. 3, 2013, Peterson.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.

* cited by examiner

TISSUE IMPEDANCE MEASUREMENT USING A SECONDARY FREQUENCY

CROSS REFERENCE TO RELATED APPLICATION

The present application is a Continuation application claiming the benefit of and priority to U.S. application Ser. No. 13/568,679, filed on Aug. 7, 2012, now U.S. Pat. No. 8,486,057 by Robert J. Behnke, entitled "TISSUE IMPEDANCE MEASUREMENT USING A SECONDARY FREQUENCY", which is a Divisional application of U.S. application Ser. No. 12/468,718, filed on May 19, 2009, now U.S. Pat. No. 8,246,615 by Robert J. Behnke, entitled "TISSUE IMPEDANCE MEASUREMENT USING A SECONDARY FREQUENCY", the entire contents of each being incorporated by reference her

BACKGROUND

1. Technical Field

The present disclosure relates generally to microwave ablation procedures that utilize microwave surgical devices having a microwave antenna which may be inserted directly into tissue for diagnosis and treatment of diseases. More particularly, the present disclosure is directed to measuring tissue impedance during a microwave ablation procedure.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 mHz to about 10 gHz is applied to a targeted tissue site to create an ablation volume, which may have a particular size and shape. Ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

Microwave ablation devices utilize thermocouples to determine when an ablation is complete. When the thermocouple reaches threshold temperature the ablation procedure is completed. Tissue impedance can also be used to determine when the ablation procedure is completed. Because ablated tissue blocks electrical signals due to non-conductive dessicated tissue, the tissue impedance can determine when the ablation procedure is completed. During application of energy, the current and voltage applied to the tissue can be measured and used to calculate impedance and the calculated impedance is stored. Based upon a function of the impedance it is determined whether the ablation procedure is complete.

During an ablation procedure, if only one antenna is used, there is no easy way to determine a change in tissue impedance. The inability to determine the change in tissue impedance is due to losses in the coaxial cable used to deliver energy to the antenna. The coaxial cable can make it difficult to measure any reflection from the antenna that could be used to determine the tissue impedance.

Additionally, antennas may use a coolant to provide improved ablation volume and shape. Any suitable medium may be used as a coolant such as deionized water, sterilized water, or saline. The coolant may have dielectric properties which may provide improved impedance matching between an antenna probe and tissue. Impedance matching is the practice of setting the probe impedance to the tissue impedance in order to maximize the power transfer and minimize reflections from the load. Due to the minimized reflections, if a water or dielectric buffer cooled antenna is used, the change in tissue impedance may be immeasurable.

SUMMARY

The present disclosure provides a microwave ablation system. The microwave ablation includes a generator including a first energy source, a second energy source and a diplexer, the diplexer operable to multiplex a first energy from the first energy source and a second energy from the second energy source. A cable is also provided that includes a center conductor and an outer sheath. The multiplexed energy is transmitted through the center conductor. Also, an antenna operable to receive the multiplexed energy from the center conductor and to deliver the multiplexed energy to a region of tissue is provided. The outer sheath acts as a return path of the second energy to the second energy source. A sensor is also provided that measures at least one parameter of the second energy generated by the second energy source and the second energy returned from the region of tissue.

The present disclosure also provides another microwave ablation system. The microwave ablation system includes a generator including a first energy source, a second energy source and a diplexer, the diplexer operable to multiplex a first energy from the first energy source and a second energy from the second energy source. A cable is also provided that includes a center conductor and an outer sheath. The multiplexed energy is transmitted through the center conductor. Also, an antenna operable to receive the multiplexed energy from the center conductor and to deliver the multiplexed energy to a region of tissue is provided. Additionally, a return pad is provided that is operable to receive the second energy outputted from the antenna. The return pad transmits the second energy to the second energy source. A sensor is also provided that measures at least one parameter of said second energy generated by said second energy source and the second energy returned from said return pad.

The present disclosure also provides a method of ablating tissue using microwave energy. The method includes generating microwave energy, generating radio frequency (RF) energy, multiplexing the microwave energy and the RF energy and outputting the multiplexed energy to a tissue region. RF energy is returned from the tissue region and at least one parameter of the generated RF energy and the RF energy returned from said tissue region is measured. Based on the measured parameter the level of microwave energy that is generated is controlled.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
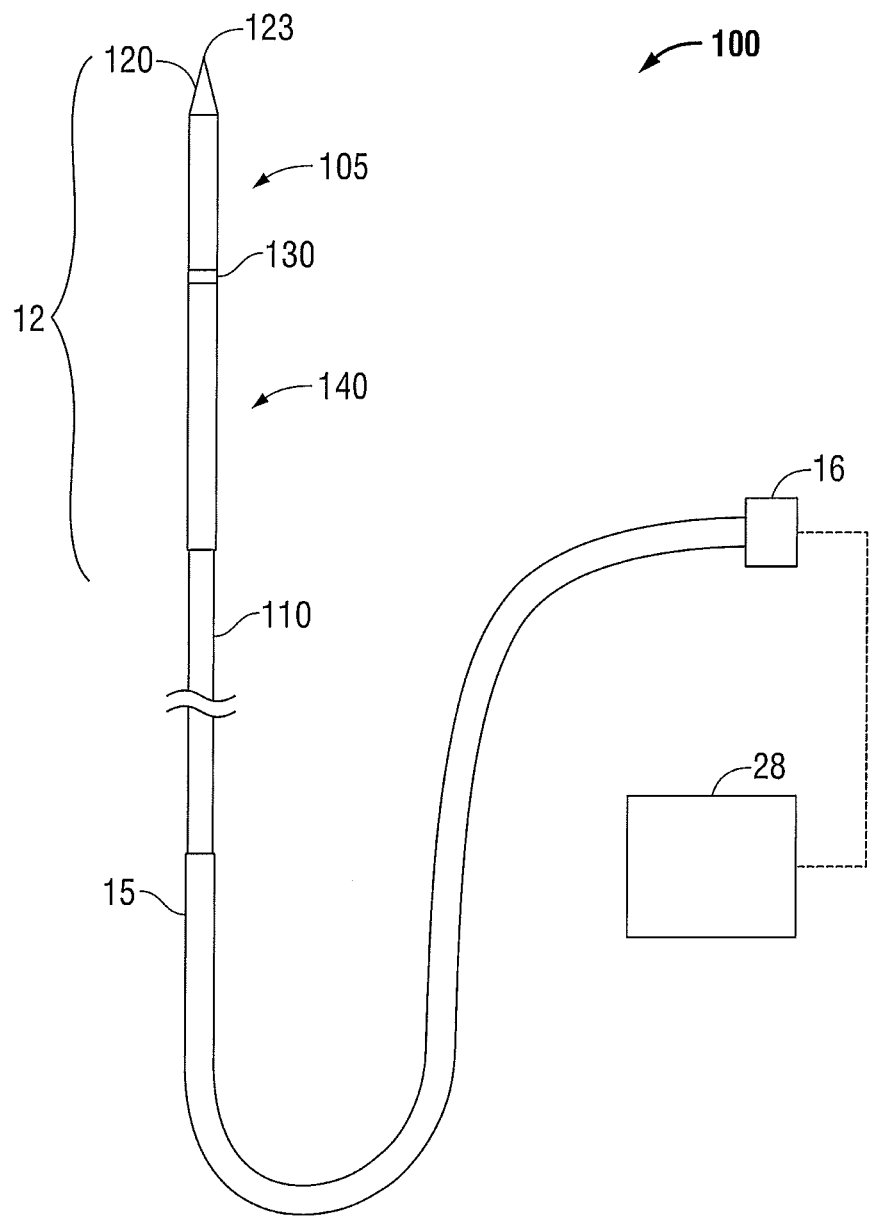
FIG. 1 shows a representative diagram of a variation of a microwave antenna assembly in accordance with an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves. The phrase "ablation procedure" generally refers to any ablation procedure, such as microwave ablation or microwave ablation assisted resection. The phrase "transmission line" generally refers to any transmission medium that can be used for the propagation of signals from one point to another.

FIG. 1 shows an embodiment of a microwave antenna assembly 100 in accordance with one embodiment of the present disclosure. Antenna assembly 100 includes a radiating portion 12 that is connected by feedline 110 (or shaft) via cable 15 to connector 16, which may further connect the assembly 10 to a power generating source 28, e.g., a microwave or RF electrosurgical generator. Assembly 100, as shown, is a dipole microwave antenna assembly, but other antenna assemblies, e.g., monopole or leaky wave antenna assemblies, may also utilize the principles set forth herein. Distal radiating portion 105 of radiating portion 12 includes a tapered end 120 which terminates at a tip 123 to allow for insertion into tissue with minimal resistance. It is to be understood, however, that tapered end 120 may include other shapes, such as without limitation, a tip 123 that is rounded, flat, square, hexagonal, or cylindroconical.

Figure 2:
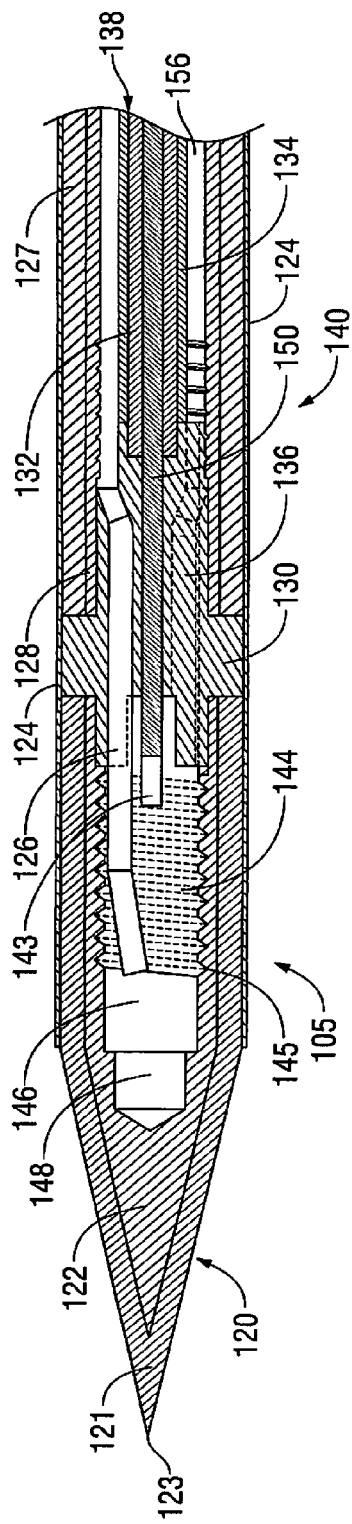
FIG. 2 shows a cross-sectional view of a representative variation of a distal end of microwave antenna assembly in accordance with an embodiment of the present disclosure.
Figure 3:
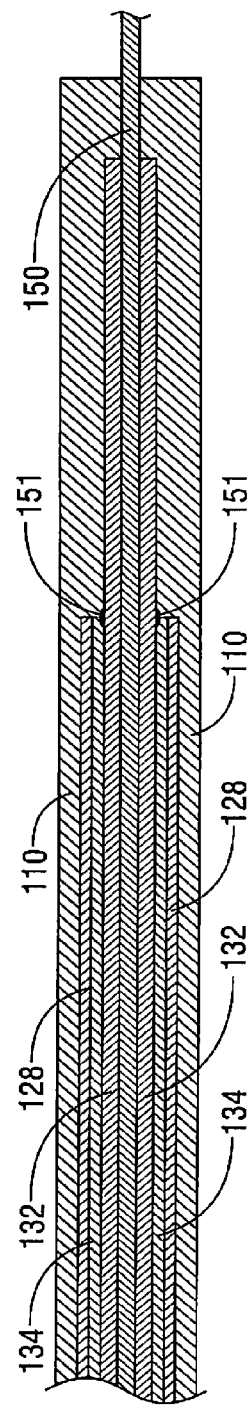
FIG. 3 shows a cross-sectional view of a representative variation of a proximal end of microwave antenna assembly in accordance with an embodiment of the present disclosure.

An insulating puck 130 is disposed between distal radiating portion 105 and proximal radiating portion 140. Puck 130 may be formed from any suitable elastomeric or ceramic dielectric material by any suitable process. In embodiments, the puck 130 is formed by overmolding from polyether block amide (e.g., Pebax®), polyetherimide (e.g., Ultem® and/or Extem®), polyimide-based polymer (e.g., Vespel®), or ceramic. As best illustrated in FIG. 2, puck 130 includes coolant inflow port 131 and coolant outflow port 133 to respectively facilitate the flow of coolant into, and out of, coolant chamber 148 of trocar 122 as further described hereinbelow.

With reference now to FIGS. 2, 3, and 4A-4D, distal radiating portion 105 includes a trocar 122 having a generally cylindroconical shape. Proximal radiating portion 140 includes a proximal antenna member 128 having a generally cylindrical shape. Additionally or alternatively, proximal antenna member 128 may have a generally square or hexagonal shape. Trocar 122 and proximal antenna member 128 may be formed from a variety of biocompatible heat resistant conductive materials suitable for penetrating tissue, such as without limitation, stainless steel. Antenna assembly 110 includes a coaxial transmission line 138 having, in coaxial disposition, an inner coaxial conductor 150, an intermediate coaxial dielectric 132, and an outer coaxial conductor 134. Nominally, coaxial transmission line 138 has an impedance of about 50 ohms. Inner coaxial conductor 150 and outer coaxial conductor 134 may be formed from any suitable electrically conductive material. In some embodiments, inner coaxial conductor 150 is formed from stainless steel and outer coaxial conductor 132 is formed from copper. Coaxial dielectric 132 may be formed from any suitable dielectric material, including without limitation, polyethylene terephthalate, polyimide, or polytetrafluoroethylene (PTFE) (e.g., Teflon®, manufactured by E. I. du Pont de Nemours and Company of Wilmington, Del., United States) Inner coaxial conductor 150 may be electrically coupled to trocar 122 and outer coaxial conductor 134 may be electrically coupled to proximal antenna member 128.

A longitudinal opening 146 is defined within trocar 122 and opens to a proximal end thereof, and defines a cooling chamber 148 and a threaded section 145 within trocar 122. Cooling chamber 148 may have a generally cylindrical shape and, additionally or alternatively, may have a stepped, tapered, conical, or other shape that is generally dimensioned in accordance with the shape of the tapered end 120 of the cylindroconical profile of trocar 122 to permit the flow of coolant to more effectively reach the distal regions of trocar 122. Additionally or alternatively, cooling chamber may have a square, hexagonal, or any suitable shape. Additionally, the dielectric properties of sterile water or saline flowing through cooling chamber 148 may enhance the overall ablation pattern of antenna 100.

A coolant inflow tube 126 is in operable fluid communication at a proximal end thereof with a source of cooling fluid (not explicitly shown), and, at a distal end thereof, coolant inflow tube 126 is in fluid communication with cooling chamber 146 to provide coolant thereto. Coolant inflow tube 126 may be formed from any suitable material, e.g., a polymeric material, such as without limitation, polyimide. In an embodiment, coolant inflow tube 126 passes through coolant inflow port 131. In some embodiments, a coolant outflow channel 136 may be provided to facilitate removal of coolant from cooling chamber 146, through antenna assembly 100, to a collection reservoir (not explicitly shown). The coolant may be any suitable fluid, such as without limitation water, sterile water, deionized water, and/or saline.

Figure 4A:
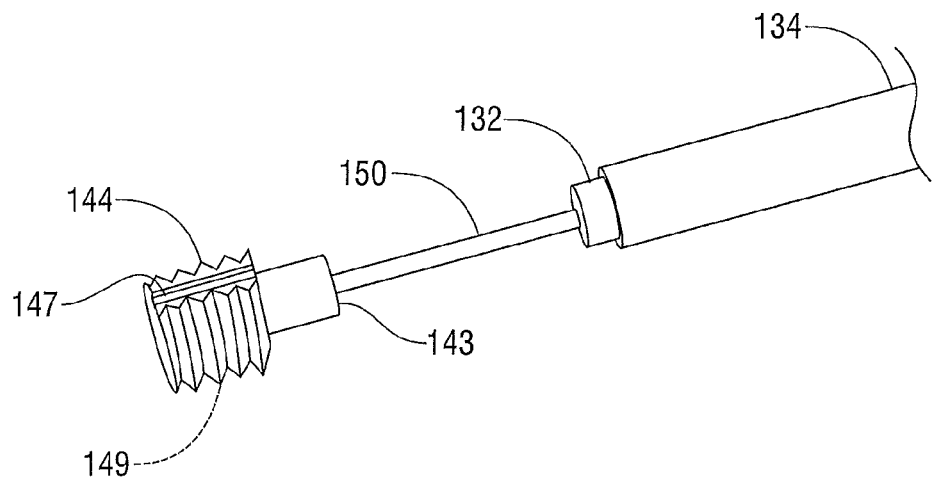
FIGS. 4A-4D show perspective views of the distal portion of a microwave antenna in various stages of assembly in accordance with an embodiment of the present disclosure.

Threaded section 145 of trocar 122 is configured to receive trocar screw 144. Trocar screw 144 includes at the proximal end thereof an opening 143 defined therein that is configured to accept the distal end of inner coaxial conductor 150. In embodiments, distal end of inner coaxial conductor 150 is fixed within opening 143 by any suitable manner of electromechanical attachment, such as without limitation welding, brazing, and/or crimping. As seen in FIG. 4A, an inflow groove 147 and an outflow groove 149 are disposed longitudinally through the threaded portion of trocar screw 144 to respectively facilitate the flow of coolant into, and out of, cooling chamber 148. Inflow groove 147 and outflow groove 149 may be configured to accommodate the insertion of coolant inflow tube 126 and/or a corresponding outflow tube (not explicitly shown). A return path 156 in the antenna assembly may additionally or alternatively provide an exit conduit for the cooling fluid.

In the illustrated embodiment, trocar 122 and proximal antenna member 128 include a dielectric coating 121, 127, respectively, on the respective outer surfaces thereof. The dielectric coating 121, 127 may include any suitable dielectric material, such as without limitation, ceramic material. In some embodiments, dielectric coating 121, 127 may be formed from titanium dioxide and/or zirconium dioxide. Dielectric coating 121, 127 may be applied to trocar 122 and/or proximal antenna member 128 by any suitable process, for example without limitation, plasma spraying or flame spraying. In embodiments, dielectric coating 121, 127 has a thickness in the range of about 0.005 inches to about 0.015 inches. During an ablation procedure, the dielectric coating 121, 127 may provide improved dielectric matching and/or improved dielectric buffering between the antenna and tissue, which may enable the use of higher power levels, which, in turn, may enable a surgeon to achieve greater ablation rates resulting in increased ablation size, reduced operative times, and/or improved operative outcomes.

An outer jacket 124 is disposed about the outer cylindrical surface of antenna assembly 100, e.g., the distal radiating portion 105, puck 130, and proximal radiating section 140. Outer jacket 124 may be formed from any suitable material, including without limitation polymeric or ceramic materials. In some embodiments, outer jacket 124 is formed from PTFE. Outer jacket 124 may be applied to antenna assembly 100 by any suitable manner, including without limitation, heat shrinking.

Continuing with reference to FIGS. 4A-4D, a method of manufacturing antenna assembly 100 is disclosed wherein inner coaxial conductor 150 is inserted into opening 143 of trocar screw 144. Inner coaxial conductor 150 is electrically fixed to trocar screw 144 by any suitable manner of bonding, such as without limitation, laser welding, brazing, or crimping. The coaxial transmission line 138 and trocar screw 144 subassembly is placed in a mold (not explicitly shown), such as without limitation an injection micro-mold, that is configured to overmold the puck 130. Advantageously, inflow groove 147 and outflow groove 149 are aligned with mold features (not explicitly shown) corresponding to coolant inflow port 131 and coolant outflow port 133 such that, when molded, a continuous fluid connection is formed between inflow groove 147 and coolant inflow port 131, and between outflow groove 149 and outflow port 133.

Figure 4B:
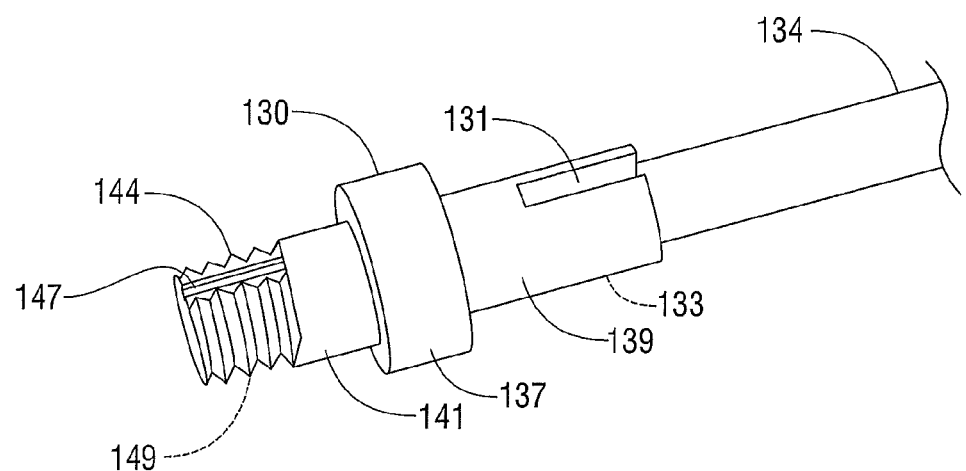

Puck material, e.g., ceramic, Pebax®, Ultem®, Extem®, Vespel®, or any suitable polymer having dielectric properties, is shot into the mold, allowed to cool/and or set, and subsequently released from the mold to form an assembly that includes puck 130, trocar screw 144 and coaxial transmission line 138 as best illustrated in FIG. 4B. The formed puck 130 includes a center section 137 having an outer diameter corresponding to the outer diameters of trocar 122 (inclusive of the thickness of dielectric coating 121) and/or proximal antenna member 128 (inclusive of the thickness of dielectric coating 127). Puck 130 further includes a distal shoulder 141 having an outer diameter corresponding to the inner diameter of trocar 122, and a proximal shoulder 139 having an outer diameter corresponding to the inner diameter of proximal antenna member 128.

Figure 4C:
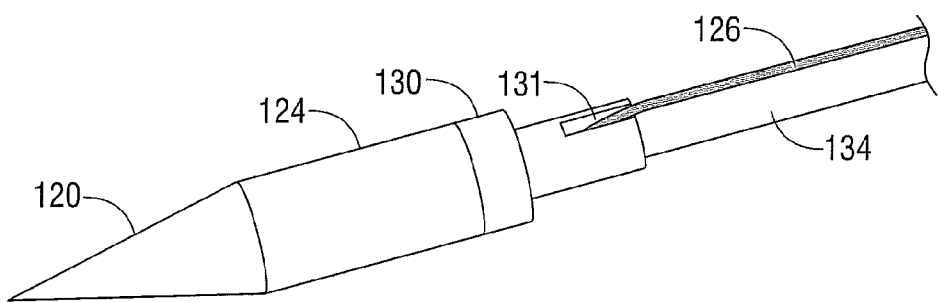
Figure 4D:
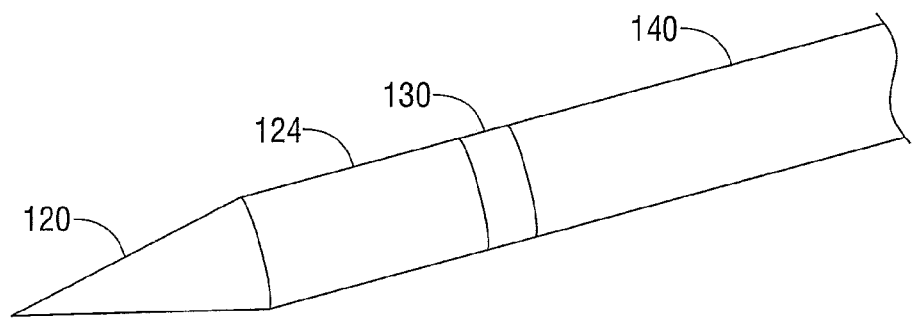

Trocar 122 may then be threaded onto trocar screw 144 to form the distal radiating section 120, as best shown in FIG. 4C. Inflow tube 126 may then be inserted into coolant inflow port 131. Proximal antenna member 128 may then be positioned against puck 130 such that the distal end of proximal antenna member 128 engages the proximal shoulder of puck 130, thus forming a sealed proximal radiation section 140.

Tension may be applied to inner coaxial conductor 150 and/or dielectric 132 in a proximal direction, thereby drawing together distal radiating section 105, puck 130, and proximal radiating section 140, and placing puck 130 in a state of compression. Inner coaxial conductor 150 and/or dielectric 132 may be fixed in a state of tension at an anchor point 151, by any suitable manner of fixation, including without limitation spot welding, brazing, adhesive, and/or crimping. In this manner, the antenna sections are "locked" together by the tensile force of inner coaxial conductor 150 and/or dielectric 132, which may result in improved strength and stiffness of the antenna assembly.

Outer jacket 124 may be applied to the outer surface of radiating portion 12 by any suitable method, for example without limitation, heat shrinking, overmolding, coating, spraying, dipping, powder coating, baking and/or film deposition.

It is contemplated that the steps of a method in accordance with the present disclosure can be performed in a different ordering than the ordering provided herein.

Figure 5:
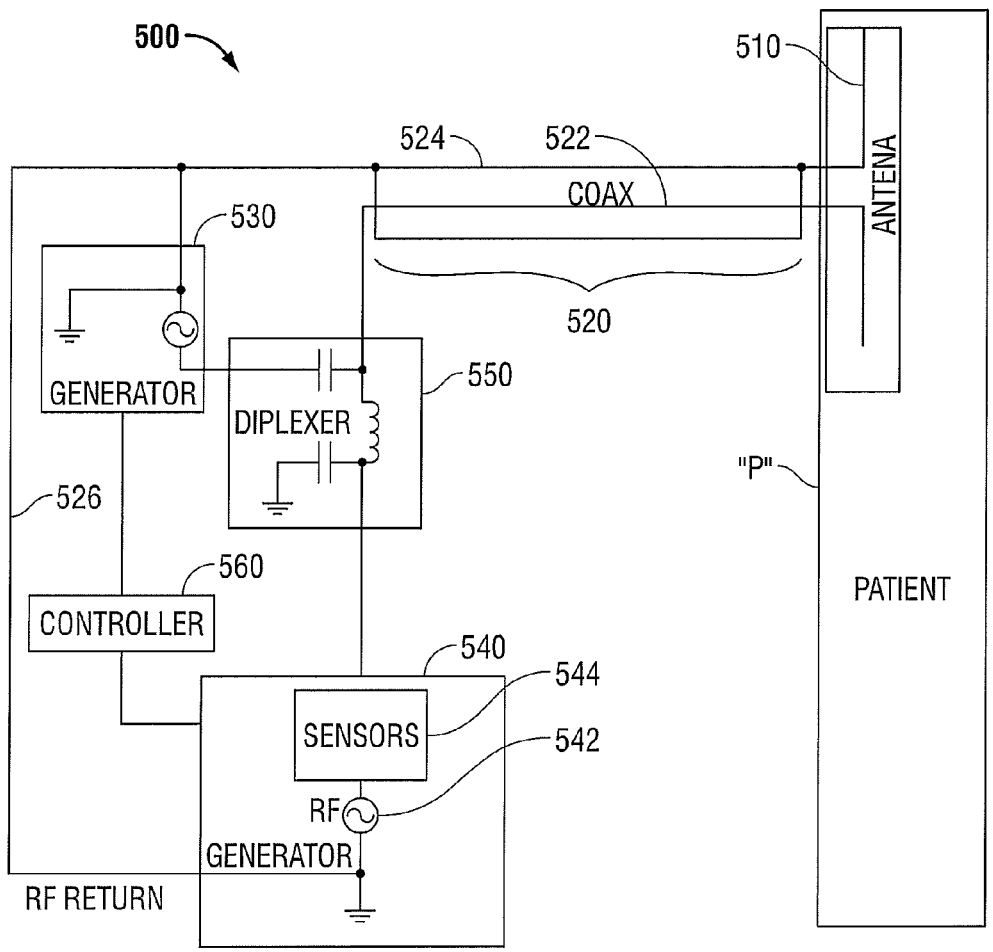
FIG. 5 is a schematic diagram of a microwave ablation system with a bipolar RF energy source according to an embodiment of the present disclosure.

FIG. 5 is a schematic illustration of a microwave system, generally shown as system 500, according to an embodiment of the present disclosure. Antenna 510 is used to ablate tissue on patient "P". Antenna 510 is coupled to coax cable 520 which has a center conductor 522 and an outer sheath 524. Outer sheath 524 is coupled to the ground terminal of microwave generator 530 which includes a microwave source 535. Outer sheath 524 is also coupled to RF generator 540 via a transmission line 526. RF generator 540 includes an RF source 542 and sensors 544. Diplexer 550 is coupled between center conductor 522 and RF generator 540. Microwave generator 530, RF generator 540 and diplexer 550 may be provided as separate units or provided in generator 28 as shown in FIG. 1.

Figure 6:
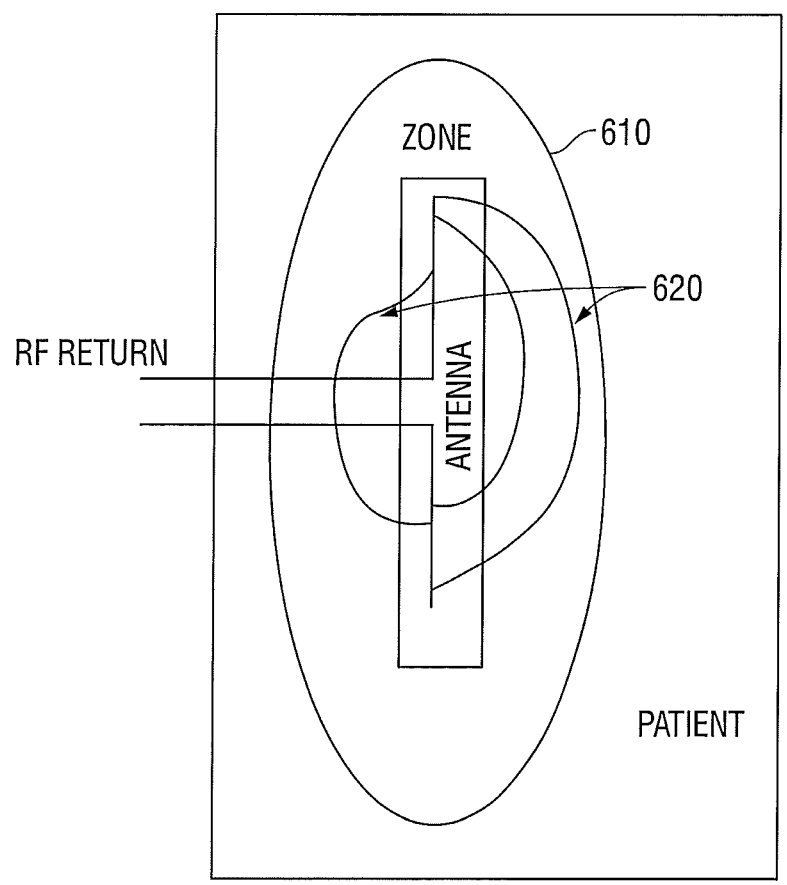
FIG. 6 is a diagram of a bipolar RF return path according to an embodiment of the present disclosure.

RF generator 540 outputs RF energy to the diplexer 550 which combines the RF energy with the microwave energy outputted by microwave generator 530. Diplexer 550 implements frequency domain multiplexing where two ports are multiplexed onto a third port. The diplexer 550 blocks the RF energy from getting into the microwave generator 530 and blocks microwave energy from getting into the RF generator 540. Diplexer 550 allows both the RF energy and the microwave energy to flow to antenna 510 simultaneously through center conductor 522. The RF energy is outputted from the antenna to the ablation zone 610 as depicted in FIG. 6. The RF path is depicted by lines 620 in FIG. 5B. The RF energy flows from antenna 510 to the ablation zone 610 and uses the same return path as the microwave energy by utilizing the outer sheath 524.

The RF energy returning from the ablation zone is used as a feedback signal and is provided to the RF generator 540 via transmission line 526. The return RF energy is combined with the RF energy provided by the RF source 542. The combined RF energy is then provided to sensors 544 which measure the voltage, current and phase of the RF energy. A sensor may be operable to measure at least one parameter of the second energy generated by the second energy source and the second energy returned from the region of tissue. Such sensors are within the purview of those skilled in the art. The measured voltage, current, and/or the phase of the RF energy, is provided to a controller 560 which calculates the tissue impedance based on the measured voltage and current. Based on the tissue impedance, the controller 560 controls the output of the microwave generator 530. Alternatively, the controller 560 can calculate the tissue impedance and display the value on a display (not shown) so that a user may control the output of the microwave generator 530 or the controller 560 can automatically adjust the output of the microwave generator by comparing the calculated tissue impedance to a predetermined impedance stored in the controller.

Figure 7:
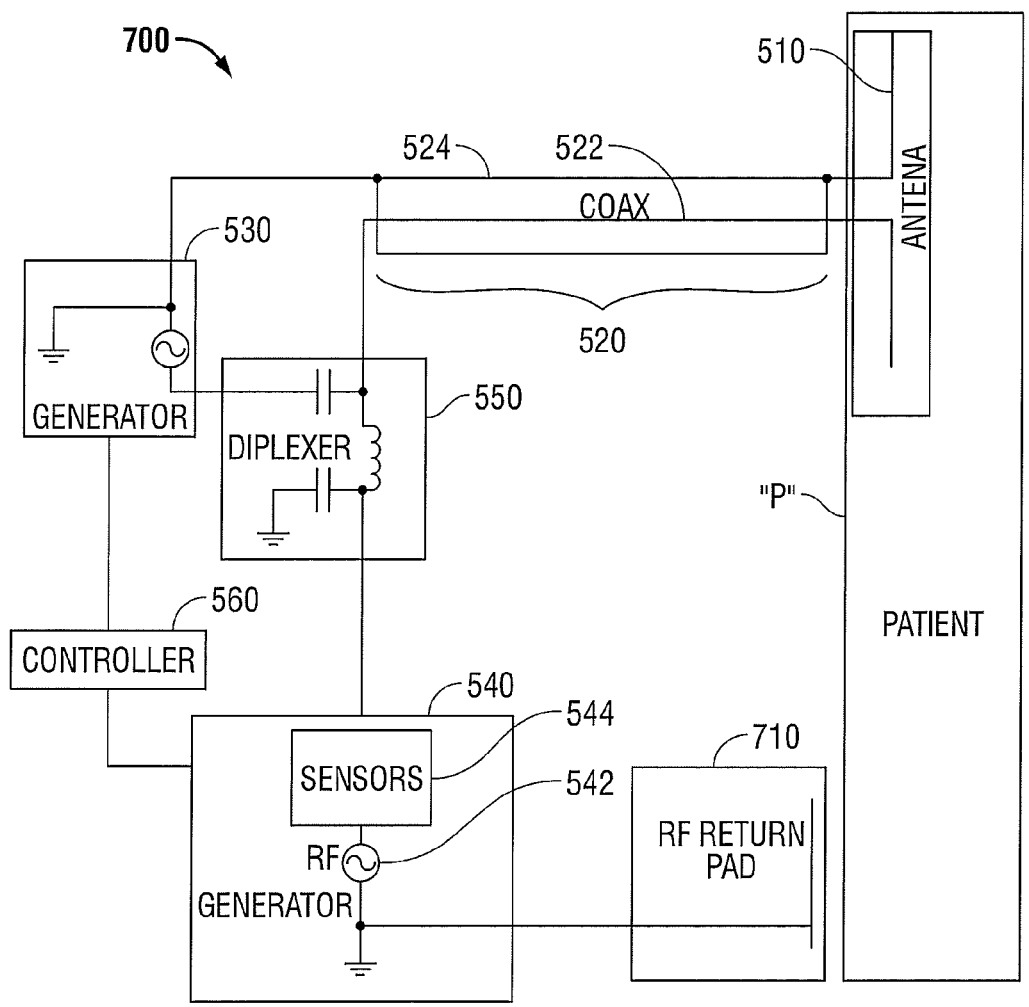
FIG. 7 is a schematic diagram of a microwave ablation system with a monopolar RF energy source according to an embodiment of the present disclosure.
Figure 8:
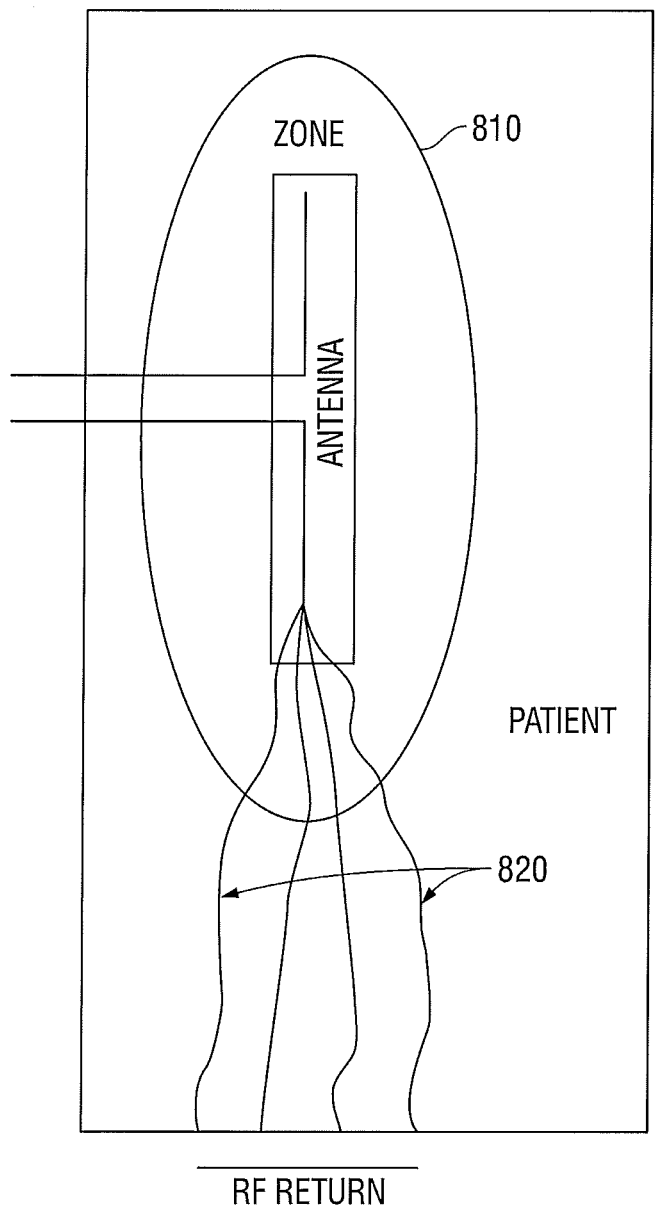
FIG. 8 is a diagram of a monopolar RF return path according to an embodiment of the present disclosure.

The controller 560 may include a microcontroller operably connected to a memory, which may be volatile type memory (e.g., RAM) and/or non-volatile type memory (e.g., flash media, disk media, etc.). The microcontroller includes an output port that is operably connected to the microwave generator 530 allowing the microcontroller to control the output of the microwave generator 530. Those skilled in the art will appreciate that the microcontroller may be substituted by any logic controller (e.g., control circuit) adapted to perform the calculations discussed herein In another embodiment according to the present disclosure, and as shown in FIG. 7, an electrosurgical system 700 is provided with an RF return pad 710 to receive a return RF signal from the ablation zone 810 as shown in FIG. 8. As shown in FIG. 8, the antenna 510 outputs RF energy in a path indicated by 820. The outputted RF energy is received by the RF return pad 810 and provided as a feedback to the RF generator 540 which is used to directly or indirectly control the microwave generator 530. The RF return pad 710 may have any suitable regular or irregular shape such as circular or polygonal. RF return pad 710 may be a conductive pad that may include a plurality of conductive arranged in a regular or irregular array. Each of the plurality of conductive elements may be equally-sized or differently-sized and may form a grid/array on the conductive pad. The plurality of conductive elements may also be arranged in a suitable spiral or radial orientation on the conductive pad. The use of the term "conductive pad" as described herein is not meant to be limiting and may indicate a variety of different pads including, but not limited to, conductive, inductive, or capacitive pads.

Although the above described embodiments describe a generator 28 having the microwave generator 530, RF generator 540, diverter 550 and controller 560, it is to be appreciated by one skilled in the art that some or all of these elements may be included in a single device or may function as separate components that are interconnected when used during an ablation procedure. Further, controller 560 may be included in the generator 28 or it may be a separate computer or laptop connected to the generator 28.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical instrument comprising:
    a connector configured to connect to an electrosurgical generator, the electrosurgical generator including a first energy source, a second energy source, and a diplexer configured to multiplex a first energy from the first energy source and a second energy from the second energy source;
    a feedline having a center conductor and an outer sheath arranged in a coaxial relationship along a longitudinal portion thereof, the feedline having a proximal end coupled to the electrosurgical generator through the connector, the center conductor configured to transmit the multiplexed energy and the outer sheath configured to act as a return path for the second energy;
    a dipole antenna including:
        a distal radiating portion having an inner conductor, the distal radiating portion including a trocar having a threaded section;
        a proximal radiating portion having an outer conductor; and
        an insulating puck disposed between the distal radiating portion and the proximal radiating portion, the insulating puck coupled to a trocar screw configured to threadably engage the threaded section of the trocar.

2. The electrosurgical instrument of claim 1, wherein the outer sheath is coupled to a ground terminal of the electrosurgical generator.

3. The electrosurgical instrument of claim 1, wherein the trocar includes a cooling chamber.

4. The electrosurgical instrument of claim 3, wherein the dipole antenna further includes a coolant inflow tube having a proximal end and a distal end, the proximal end configured to be in fluid communication with a source of cooling fluid, and the distal end in fluid communication with the cooling chamber.

5. The electrosurgical instrument of claim 4, wherein the trocar screw includes an inflow groove disposed longitudinally thereon and configured to receive the coolant inflow tube.

* * * * *